United States Patent
Wakui et al.

(10) Patent No.: US 9,829,430 B2
(45) Date of Patent: Nov. 28, 2017

(54) SPECTROPHOTOMETER

(71) Applicant: Hitachi High-Technologies Corporation, Tokyo (JP)

(72) Inventors: Takayuki Wakui, Tokyo (JP); Hayato Tobe, Tokyo (JP); Koichi Nakamura, Tokyo (JP); Koji Yamamoto, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 354 days.

(21) Appl. No.: 14/422,276

(22) PCT Filed: Jul. 22, 2013

(86) PCT No.: PCT/JP2013/069723
§ 371 (c)(1),
(2) Date: Feb. 18, 2015

(87) PCT Pub. No.: WO2014/030475
PCT Pub. Date: Feb. 27, 2014

(65) Prior Publication Data
US 2015/0247793 A1   Sep. 3, 2015

(30) Foreign Application Priority Data
Aug. 20, 2012 (JP) .................................. 2012-181302

(51) Int. Cl.
*G01N 21/00* (2006.01)
*G01N 21/31* (2006.01)
(Continued)

(52) U.S. Cl.
CPC ............ *G01N 21/31* (2013.01); *G01J 3/0291* (2013.01); *G01J 3/42* (2013.01); *G01N 21/01* (2013.01);
(Continued)

(58) Field of Classification Search
None
See application file for complete search history.

(56) References Cited

U.S. PATENT DOCUMENTS 3,591,289 A * 7/1971 Donega .............. G01N 21/3103
356/244
3,721,824 A * 3/1973 Bristol .................. G01T 1/2045
250/207
(Continued)

FOREIGN PATENT DOCUMENTS

JP          6449940       2/1989
JP          1137940       2/1999
(Continued)

OTHER PUBLICATIONS

International Search Report in PCT/JP2013/069723, dated Sep. 10, 2013.

*Primary Examiner* — Tri Ton
*Assistant Examiner* — Jarreas C Underwood
(74) *Attorney, Agent, or Firm* — Mattingly & Malur, PC

(57) ABSTRACT

A spectrophotometer includes: a sample-chamber lid capable of opening and closing an opening portion of a sample chamber for setting a sample and a reference sample; and sample-chamber lid opening-closing detecting means for detecting an opening-closing state of the sample-chamber lid, and the spectrophotometer is capable of controlling a measurement of a xenon flash tube as a light source, a spectroscope, a detector, an amplifier, an AD converter, a processor, a storage device, and a data display part. In the spectrophotometer, the light source is turned on after a state of the lid changing from an opening state to a closing state is detected in a sample-setting instruction state by the sample-chamber lid opening-closing detecting means; absorbancy, transmissivity, reflectivity, a sample-side energy value, or a reference-side energy value is measured; and a measurement result is displayed on the data display part.

6 Claims, 7 Drawing Sheets

(51) Int. Cl.
*G01J 3/42* (2006.01)
*G01N 21/27* (2006.01)
*G01J 3/02* (2006.01)
*G01N 21/01* (2006.01)

(52) U.S. Cl.
CPC ... *G01N 21/274* (2013.01); *G01N 2201/0253* (2013.01); *G01N 2201/062* (2013.01); *G01N 2201/126* (2013.01)

(56) References Cited

U.S. PATENT DOCUMENTS

| | | | | |
|---|---|---|---|---|
| 4,502,786 | A | * | 3/1985 | Golias ............ G01N 21/27 356/40 |
| 4,840,484 | A | * | 6/1989 | Oishi ............ G01N 21/74 356/312 |
| 5,785,960 | A | * | 7/1998 | Rigg ............ A45D 44/005 366/160.1 |
| 6,262,798 | B1 | * | 7/2001 | Shepherd ............ G01N 21/31 356/39 |
| 6,600,558 | B2 | * | 7/2003 | Ueno ............ G01N 21/0332 356/244 |
| 8,208,145 | B2 | * | 6/2012 | Large ............ G01N 21/03 356/246 |
| 2015/0142364 | A1 | * | 5/2015 | Workman ............ G01N 21/274 702/104 |

FOREIGN PATENT DOCUMENTS

| | | |
|---|---|---|
| JP | 2005095134 | 4/2005 |
| JP | 2005147811 | 6/2005 |
| JP | 2005201680 | 7/2005 |
| JP | 2006162259 | 6/2006 |
| JP | 2008070274 | 3/2008 |

* cited by examiner

ELAPSED TIME FROM CLOSING OF THE SAMPLE-CHAMBER LID (s)

ELAPSED TIME FROM CLOSING OF THE SAMPLE-CHAMBER LID (s)

SPECTROPHOTOMETER

TECHNICAL FIELD

The present invention relates to a spectrophotometer, more particularly, to spectrophotometer that mounts sample-chamber lid opening-closing detecting means.

BACKGROUND

Until now, techniques of mounting sample-chamber-lid opening-closing detecting means on a sample chamber or a sample-chamber lid of a spectrophotometer, and using the same have been known in Patent Documents 1, 2, and 3.

The spectrophotometer disclosed in Patent Document 1 is a method of providing sample-chamber lid opening-closing detecting means to a lid of a sample chamber to let light flux enter the sample chamber and block such light flux entering the sample chamber. This method targets a spectrophotometer using a deuterium lamp and a tungsten lamp as its light sources. The heat-generation amounts of the deuterium lamp and tungsten lamp are high. Thus, when the light source is once turned off, time is required to stabilize the light source. Therefore, according to this patent, the light source itself is not turned off and a slit plate or a light source mirror blocks light flux from the light source. Accordingly, the method disclosed in Patent Document 1 does not contribute to increasing of usable period of the light source and reducing in power consumption of an apparatus.

The nucleic acid detecting apparatus disclosed in Patent Document 2 includes closing lid means that closes a lid of a detecting container and means for amplifying and detecting target nucleic acid in the closed detecting container after dispensing of a reagent and a sample. According to the technique disclosed in Patent Document 2, after the lid is closed, a pre-process of amplifying a target gene by gene amplification reaction is performed and thus the measurement is not started by closing the lid. This is because the act of closing the lid is aimed for preventing contamination of the sample. Therefore, in the method disclosed in Patent Document 2, increase of usable period and reduction in power consumption of an apparatus are not considered.

The spectrophotometer disclosed in Patent Document 3 is characterized in providing detecting means capable of detecting whether a sample is set at a sample-setting place of a sample chamber and another detecting means capable of detecting opening and closing of the sample chamber, and automatically acquiring background data in a state in which the sample chamber is closed and in a state in which a sample is not set. However, as the technique disclosed in Patent Document 3 does not include a technique of controlling opening and closing of a lid of the sample chamber and controlling turning on and off of a light source. Thus, the Patent Document 3 does not contribute to increasing of usable period and reducing in power consumption of an apparatus.

PRIOR ART DOCUMENTS

Patent Documents

Patent Document 1: Japanese Patent Application Laid-Open Publication No. 2005-201680
Patent Document 2: Japanese Patent Application Laid-Open Publication No. 2005-95134
Patent Document 3: Japanese Patent Application Laid-Open Publication No. 2006-162259

SUMMARY

Problems to be Solved by the Invention

The above-described existing techniques are on the premise of a spectrophotometer having a deuterium lamp and a tungsten lamp as its light sources. In such a spectrophotometer, the heat generation amounts of the light sources are high. Thus, when the light source is once turned off, time is required to stabilize the light sources. Therefore, the light sources have been used always in an on-state even in a usage period except for a measurement period, such as setting of a sample. Because of that, there have been such problems that it is difficult to effectively use light from the light source in addition to that power consumption is high.

The present invention is aimed for achieving increase of a usable period of a light source and reduction in power consumption of an apparatus by using light from a light source of a spectrophotometer, effectively.

Means for Solving the Problems

A spectrophotometer includes: a sample-chamber lid capable of opening and closing an opening portion of a sample chamber for setting a sample and a reference sample; and sample-chamber lid opening-closing detecting means for detecting an opening-closing state of the sample-chamber lid, and the spectrophotometer is capable of controlling a measurement of a xenon flash tube as a light source, a spectroscope, a detector, an amplifier, an AD converter, a processor, a storage device, and a data display part. In the spectrophotometer, the light source is turned on after detecting a state of the lid changing from an opening state to a closing state in a sample-setting instruction state by the sample-chamber lid opening-closing detecting means; absorbancy, transmissivity, reflectivity, a sample-side energy value, or a reference-side energy value is measured; and a measurement result is displayed on the data display part.

Effects of the Invention

According to the present invention, by controlling turning on and off of a light source in cooperation with the sample-chamber lid, effects of increase of a usable period of the light source and reduction in power consumption of an apparatus are obtained.

DETAILED DESCRIPTION

Hereinafter, embodiments of the present invention will be described with reference to the drawings.

Figure 1:
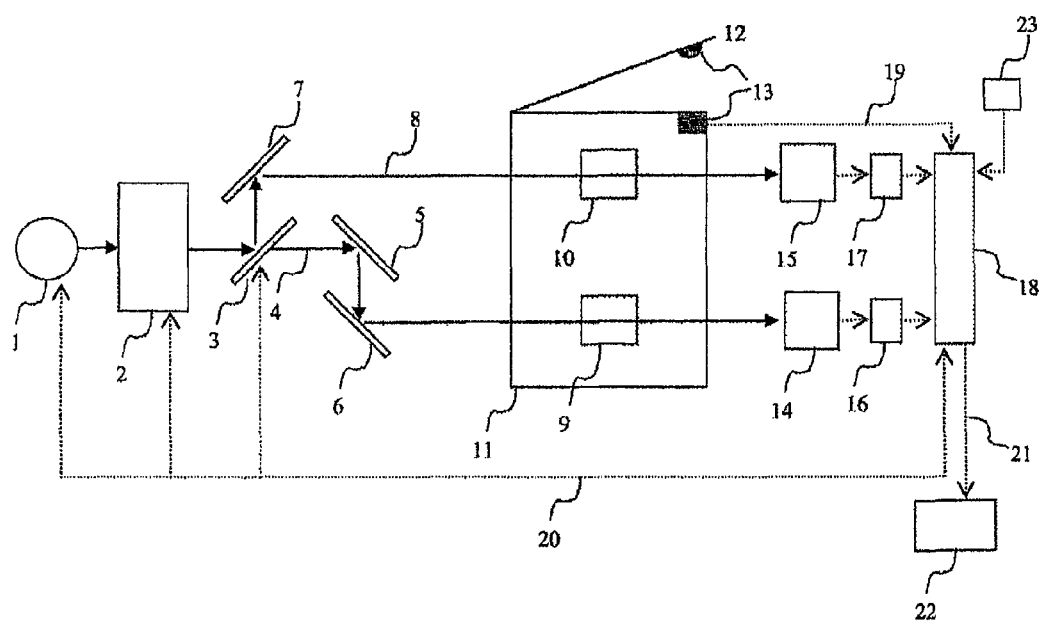
FIG. 1 is a diagram illustrating a configuration of a spectrophotometer and flows of signal processing of the same.

FIG. 1 is a diagram illustrating a configuration of a spectrophotometer and flows of signal processing of the same. White light indicated by a solid arrow emitted from a light source 1 is dispersed to extract a specific wavelength by a spectrometer 2, and separated into a sample-side light flux 4 and a reference-side light flux 9 by a beam splitter 3. The light fluxes are reflected by reflecting mirrors 5, 6 and 7 and guided to a sample chamber 11. In the sample chamber 11, the sample-side light flux 4 passes through a sample that is set in a sample setting part 9 and transmitted light of a sample is detected by a sample-side detector 14.

On the other hand, a reference-side light flux 8 passes through a reference sample that is set in a reference-sample setting part 10 and detected by a reference-side detector 15. Here, by irradiating light having the wavelength optionally selected by the spectrometer 2 on the sample and measuring an amount of the transmitted light by the sample-side detector 14 based on a light amount detected by the reference-side detector 15, absorbed, transmitted, or reflected amount of light in the sample can be learned. For example, in the case of an absorbance measurement of a solution measurement, a measuring person can learn a concentration of an unknown sample by comparing an absorbancy obtained from a solution sample containing a component at a known concentration and an absorbancy of a sample having unknown concentration.

Although FIG. 1 shows a configuration of a so-called double beam system in which a light flux is divided to the sample side and reference side, the present invention can also be performed in a single beam system having no reference-side light flux and a ratio beam system having no reference-sample setting part.

Flows of a signal processing according to the present invention are indicated by dotted arrows. The light fluxes detected by the sample-side detector 14 and the reference-side detector 15 are converted to electric signals and then amplified by a sample-side AMP/AD converter 16 and a reference-side AMP/AD converter 17, respectively, thereby converting analog signals into digital signals. The digital signals are subjected to calculations of absorbancy, transmissivity, reflectivity, a sample-side energy value, and a reference-side energy value by a processor/storage device 18. By instruction-inputting means 23, a measuring person can input instructions such as conditions for operating the spectrophotometer. The processor/storage device 18 performs control of the light source 1, the spectrometer 2, and the beam splitter 3, referring to apparatus control signals, in accordance with the input for instructions inputted by instruction-inputting means. Further, signals of detecting opening-closing of the sample-chamber lid 12 by the sample-chamber lid opening-closing detecting means 13 are inputted into the processor/storage device 18 as detection signals of opening-closing of sample-chamber lid 19, and the opening-closing state of the sample-chamber lid 12 can be used in control of the apparatus. As a sensor used in the sample-chamber lid opening-closing detecting means 13, a photo interrupter, a microswitch, a hall sensor, etc. can be used. Information processed in the processor/storage device 18 is displayed on a display part 22 according to display signals 21. In this manner, the measuring person can learn information of the measurement results and states of the apparatus.

In general spectrophotometers, a deuterium lamp and a tungsten iodine lamp are used as the light source 1. However, since the amounts of heat generation of these lamps are high, light amount is not stabilized until the lamps reach thermal equilibria and a phenomenon (drift) of fluctuation of a baseline occurs. Thus, immediately after turning on the lamps like upon starting up the apparatus, they cannot be used in a measurement and a certain standby time has been required. Therefore, until the last measurement is ended, the lamps turned on upon starting up the apparatus could have never been turned off. This has restricted reduction in power consumption of the apparatus and life-increase of the lamps.

However, in recent year, a xenon flash tube has been introduced to be used as a lamp in spectrophotometers. The xenon flash tube has advantages of enabling pulse lighting (intermittent lighting) and low heat generation. For such advantages, with the use of the xenon flash tube, it is possible to turn on and off the lamp as needed in the measurement and to control turning on and off of the lamp finely depending on the situation. Further, the opening-closing information of the sample-chamber lid 12 detected by the sample-chamber lid opening-closing detecting means 13 is used in control of turning on and off of the lamp. For example, although the already-existing light sources have continuously turned on from the start-up of the apparatus until a measurement ends, in the present invention, turning-on of the light source is interrupted when the sample-chamber lid inside which a sample is set is opened. In this manner, the life of lamp is enhanced and power consumption is reduced.

Figure 2:
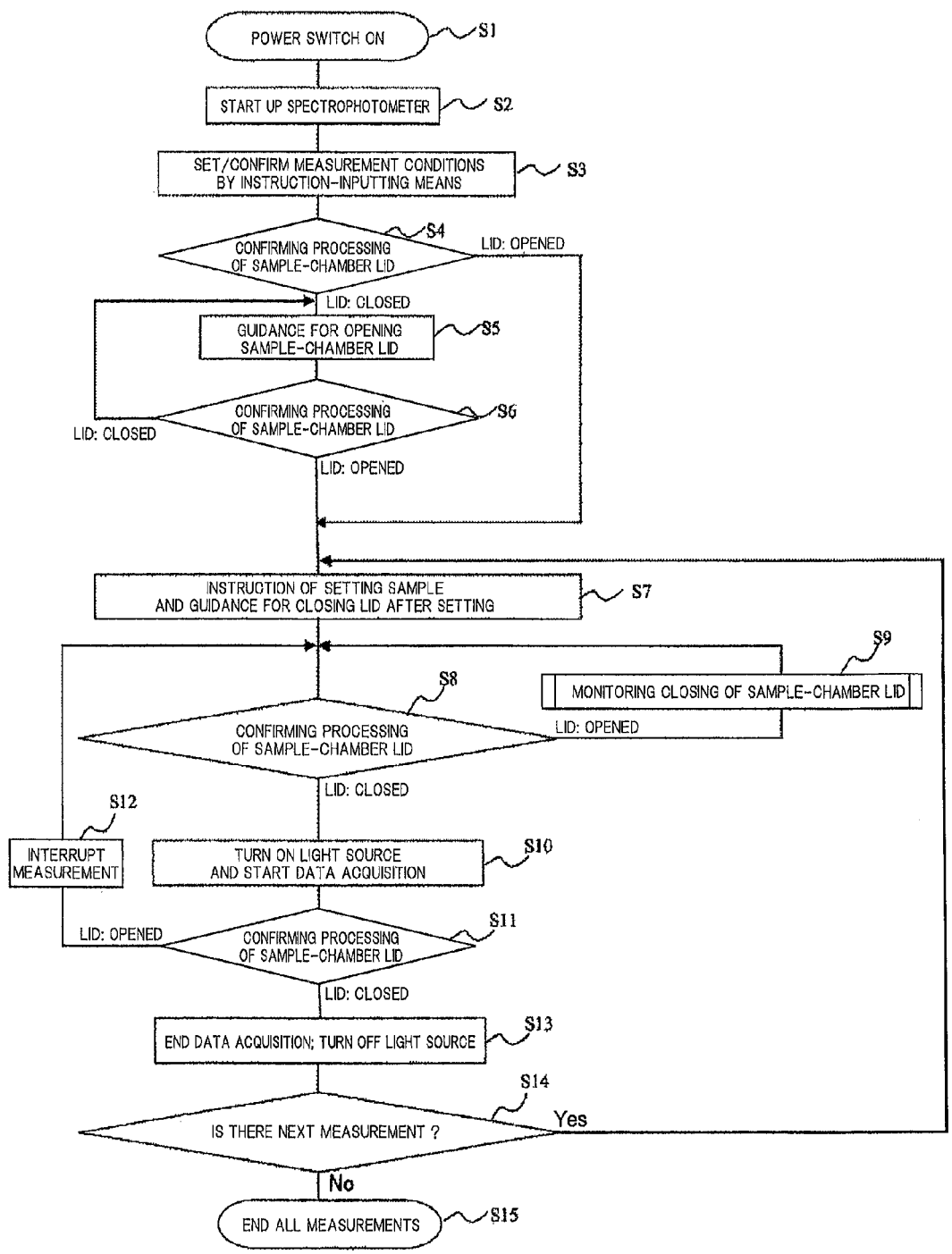
FIG. 2 is a flowchart of a control processing executed by a processor/storage device according to a first embodiment of the present invention.

FIG. 2 is a flowchart of a measurement control processing executed by a processor/storage device according to a first embodiment of the present invention. Hereinafter, the drawing will be explained.

(Step S1) A power switch (illustration omitted) is turned on.

(Step S2) The spectrophotometer is started up, and the light source 1, the spectrometer 2, the beam splitter 3, the sample-side detector 14, the reference-side detector 15, the sample-side AMP/AD converter 16, the reference-side AMP/AD converter 17, the processor/storage device 18, and the display part 22 are shifted into operating states to start an apparatus-control processing.

(Step S3) The measuring person inputs and confirms measurement conditions for operating the spectrophotometer such as a wavelength and measurement cycles by the instruction-inputting means 23 in accordance with a measured sample. In this manner, the light source 1, spectrometer 2, and beam splitter 3 are set to desired conditions.

(Step S4) Here, according to opening-closing information of the sample-chamber lid obtained from the sample-chamber lid opening-closing detecting means 13, when the sample-chamber lid is closed, the process goes to Step S5, and when the sample-chamber lid is opened, the process goes to Step S7.

(Step S5) The sample-chamber lid is opened, and guidance for opening the sample-chamber lid is displayed to prompt the measuring person to set the measured sample. The measuring person sets an actual sample or a sample for correcting a measured value to zero absorbancy or for correcting transmissivity and reflectivity to 100% following the guidance.

(Step S6) According to the opening-closing information of the sample-chamber lid obtained from the sample-chamber lid opening-closing detecting means 13, when the sample-chamber lid is closed, the process goes back to Step S5, and when the sample-chamber lid is opened, the process goes to Step S7.

(Step S7) For the measuring person, guidance for setting a sample and closing the sample-chamber lid after setting the sample is displayed.

(Step S8) As the measuring person sets a sample in the sample chamber and closes the sample-chamber lid, the opening-closing information detected by the sample-chamber lid opening-closing detecting means 13 is shifted to closing, thereby going to Step S10. When the sample-chamber lid is in an opening state, the process goes to Step S9.

(Step S9) Closing of the sample-chamber lid is monitored using the sample-chamber lid opening-closing detecting means 13.

(Step S10) The light source is turned on and data acquisition is started.

(Step S11) Whether the measuring person opens the sample-chamber lid during a measurement or not is monitored using by the sample-chamber lid opening-closing detecting means 13. When the sample-chamber lid is opened, the process goes to Step S12. When the sample-chamber lid is kept in a closing state until the measurement ends, the process goes to Step S13.

(Step S12) When the sample-chamber lid is opened during the measurement, since a detected amount is fluctuated as illumination light outside the apparatus enters the sample-side detector 14 and the reference-side detector 15 via the sample chamber and thus a measured light value of the sample cannot be correctly obtained, and the measurement is interrupted. Then, the process returns to Step S8 to monitor closing of the sample-chamber lid. When the sample-chamber lid is closed, the measurement is performed again.

(Step S13) After predetermined data acquisition is ended, the light source is turned off.

(Step S14) When there is a next measurement according to the measurement conditions set in Step S3, the process returns to Step S7. When there is no next measurement, the process goes to Step S15.

(Step S15) Measurement is ended.

In the above-described manner, with use of the freely designable xenon flash tube that is capable of turning on and off a light source and the sample-chamber lid opening-closing detecting means 13 in combination, turning-on time of the lamp can be reduced by turning off the lamp in the state in which the sample-chamber lid is opened, and power consumption can be reduced. The sequence illustrated in FIG. 2 can be used in a quantitative measurement of measuring a measured value of a single or a plurality of fixed wavelength(s), a measurement of scanning wavelength such as an absorbance spectrum, transmission spectrum, reflection spectrum, and a time change measurement of monitoring change of a measured value over time.

Figure 3:
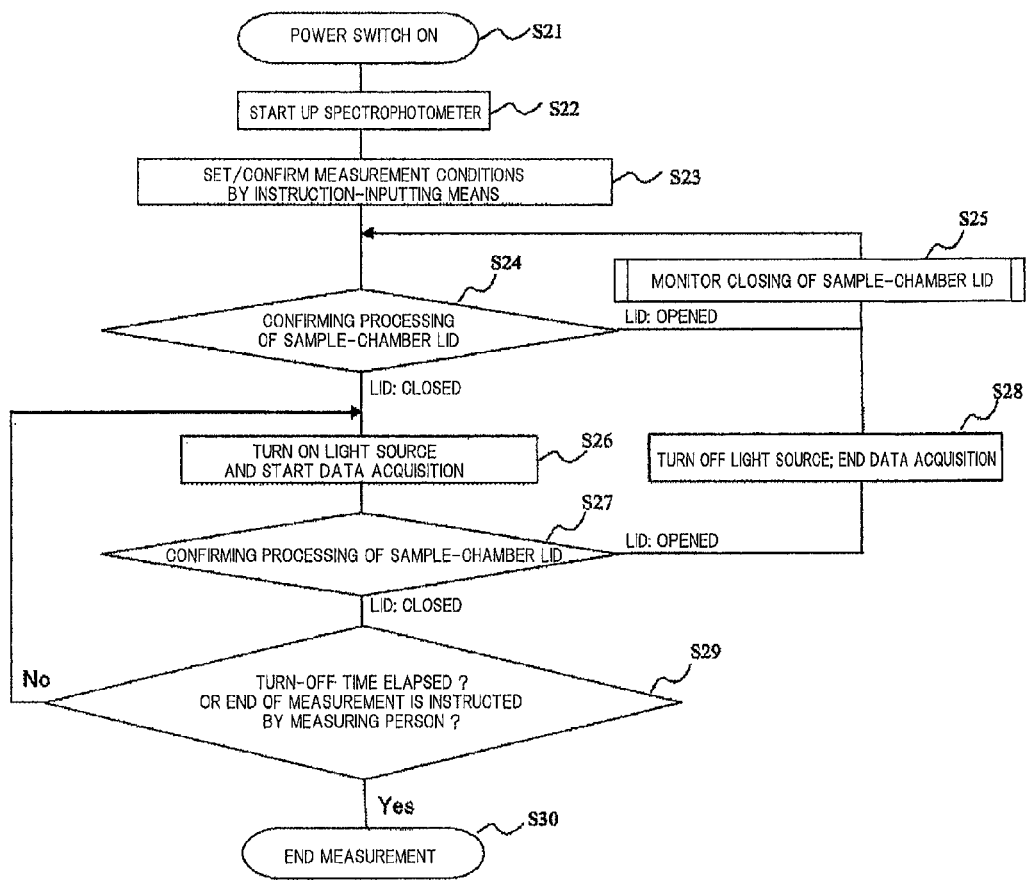
FIG. 3 is a flowchart of a control processing executed by a processor/storage device according to a second embodiment of the present invention.

FIG. 3 is a flowchart of a measurement control processing executed by a processor/storage device according to a second embodiment of the present invention. Hereinafter, the drawing will be explained.

(Step S21) A power switch (illustration omitted) is turned on.

(Step S22) The spectrophotometer is started up, and the light source 1, the spectrometer 2, the beam splitter 3, the sample-side detector 14, the reference-side detector 15, the sample-side AMP/AD converter 16, the reference-side AMP/AD converter 17, the processor/storage device 18, and the display part 22 are shifted into operating states to start an apparatus-control processing.

(Step S23) The measuring person inputs and confirms measurement conditions for operating the spectrophotometer such as a wavelength and measurement cycles by the instruction-inputting means 23 in accordance with a measured sample. In this manner, the light source 1, spectrometer 2, and beam splitter 3 are set to desired conditions.

(Step S24) Here, according to opening-closing information of the sample-chamber lid obtained from the sample-chamber lid opening-closing detecting means 13, when the sample-chamber lid is closed, the process goes to Step S26, and when the sample-chamber lid is opened, the process goes to Step S25.

(Step S25) When the sample-chamber lid is being opened, using opening-closing information of the sample-chamber lid obtained by the sample-chamber lid opening-closing detecting means 13, closing of the sample-chamber lid is monitored. Here, guidance for closing the sample-chamber lid may be displayed to prompt the measuring person to close the sample-chamber lid.

(Step S26) The light source is turned on and data is acquired.

(Step S27) During turning-on of the light source, whether the sample-chamber lid is being closed or not is monitored. When the sample-chamber lid is opened during turning-on of the light source, the process goes to Step S28. When the sample-chamber lid is being closed, the process goes to Step S29.

(Step S28) When the sample-chamber lid is being opened, because of influences from illumination light from outside, the light source is turned off and the data acquisition is ended. Then, closing of the sample-chamber lid is monitored, and when the sample-chamber lid is closed again, the light source is turned on and data is acquired.

(Step S29) When the measuring person pushes a button for ending the measurement during the measurement, the process goes to Step S30 and the measurement is ended. Also, when a turning-off time of the light source set in the measurement conditions of Step S23 has elapsed, the process goes to Step S30 and the measurement is ended. This function is aimed for preventing wasting of the lamp if the measuring person forgets the instructions for ending the measurement. Except for the instructions of ending the measurement and the elapse of the turning-off time of the light source, the process goes to the processing of Step S26 to continue turning-on of the light source and the data acquisition.

(Step S30) The measurement is ended.

The sequence illustrated in FIG. 3 can be used in a measurement of reading a monitor value. The measurement of reading a monitor value displays an obtained measured light value on the display part 22 as needed and reads the measured light value after setting a sample in the sample chamber at any timing of the measuring person. Since a measured value can be obtained easily by this measurement even when the measuring person does not know how to use the apparatus in detail, this measurement is designed for beginners of the apparatus. Through the sequence illustrated in FIG. 3, by the sample-chamber lid opening-closing detecting means 13 and control of turning on and off of the xenon flash tube, the measurement is interrupted by turning off the lamp in a state that the sample chamber is being opened upon replacing samples, wasting of the lamp is prevented and thus power consumption can be lowered.

For example, assuming that 50% of time is spent on preparation and setting of the samples from the start to the end of whole the measurements when absorbancy measurements are performed on 100 samples, a turning-on time and power consumption of the lamp were simulated in the case of measuring by a spectrophotometer consuming power at 35 W when the lamp is being turned on and at 30 W when the lamp is being turned off. As a result, the turning-on time in the case of turning on and off the lamp was half of that in the case of always turning on the lamp; thus, the lifetime of the lamp was able to be doubled. In addition, as to power consumption, in the case of controlling turning on and off of the lamp, the power consumption was able to be reduced by 7.1% as compared to the case of always turning on the lamp. In this manner, by controlling turning on and off of the lamp, the lifetime can be enhanced by preventing wasting of the lamp, and the power consumption can be reduced by 7.1%.

Figure 4:
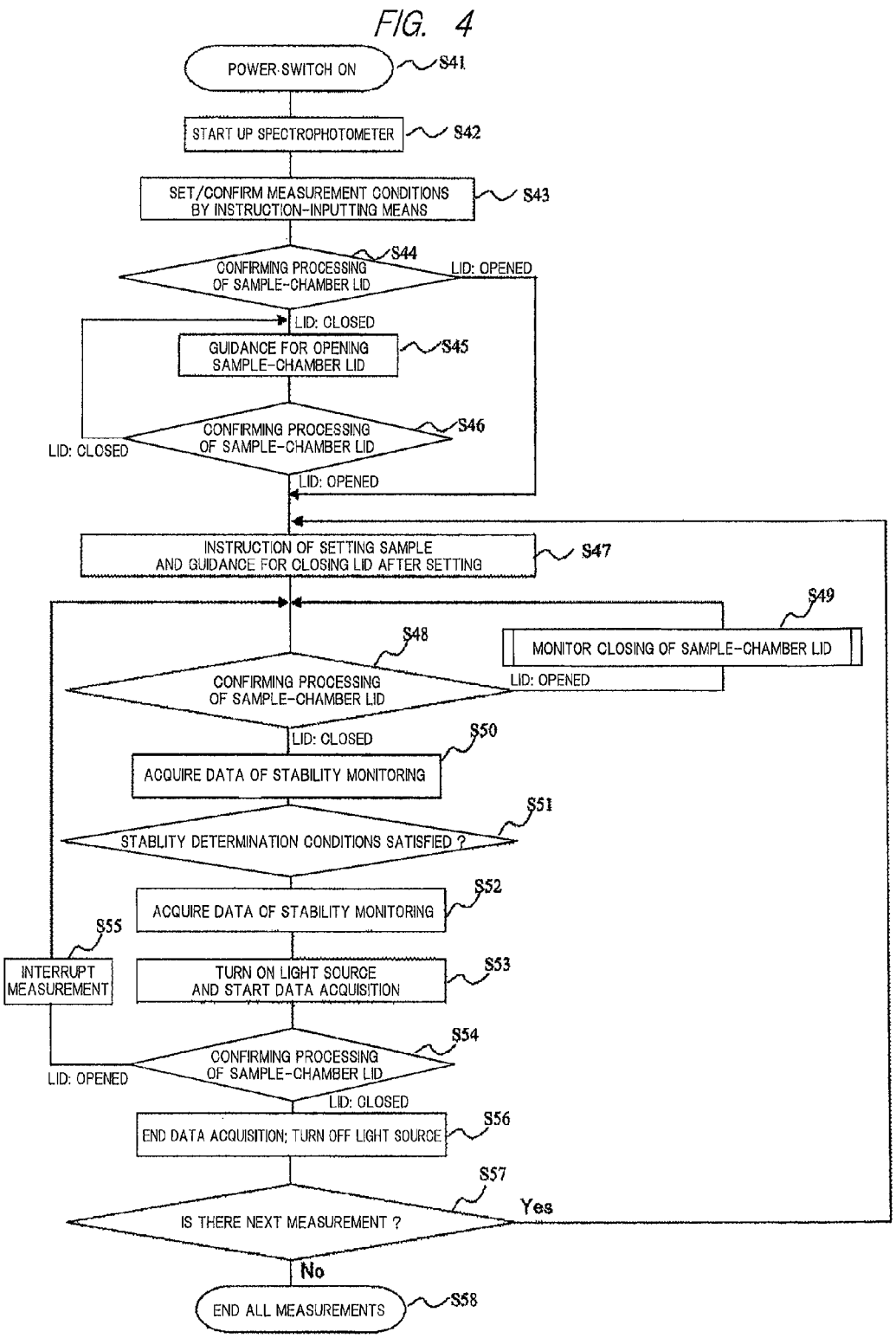
FIG. 4 is a flowchart of a control processing executed by a processor/storage device according to a third embodiment of the present invention.

FIG. 4 is a flowchart of a measurement control processing executed by a processor/storage device according to a third embodiment of the present invention. Hereinafter, the drawing will be explained.

(Step S41) A power switch (illustration omitted) is turned on.

(Step S42) The spectrophotometer is started up, and the light source 1, the spectrometer 2, the beam splitter 3, the sample-side detector 14, the reference-side detector 15, the sample-side AMP/AD converter 16, the reference-side AMP/AD converter 17, the processor/storage device 18, and the display part 22 are shifted into operating states to start an apparatus-control processing.

(Step S43) The measuring person inputs and confirms measurement conditions for operating the spectrophotometer such as a wavelength and measurement cycles by the instruction-inputting means 23 in accordance with a measured sample. In this manner, the light source 1, spectrometer 2, and beam splitter 3 are set to desired conditions. In Step S8 of the first embodiment, there is such a problem that the measured value is not stabilized when the sample-chamber lid opening-closing detecting means 13 measures the absorbancy, transmissivity, reflectivity, etc. immediately after detecting that the sample-chamber lid is closed. To solve this problem, stability determination conditions are confirmed by inputting an upper-limit value and a lower-limit value of stability determination conditions by the instruction-inputting means 23, and data acquisition is started at a time a value within the stability determination conditions is obtained.

(Step S44) Here, according to opening-closing information of the sample-chamber lid obtained from the sample-chamber lid opening-closing detecting means 13, when the sample-chamber lid is closed, the process goes to Step S45, and when the sample-chamber lid is opened, the process goes to Step S47.

(Step S45) The sample-chamber lid is opened, and guidance for opening the sample-chamber lid is displayed to prompt the measuring person to set the measured sample. The measuring person sets an actual sample or a sample for correcting a measured value to zero absorbancy or for correcting transmissivity and reflectivity to 100% following the guidance.

(Step S46) According to the opening-closing information of the sample-chamber lid obtained from the sample-chamber lid opening-closing detecting means 13, when the sample-chamber lid is closed, the process goes back to Step S45, and when the sample-chamber lid is opened, the process goes to Step S47.

(Step S47) For the measuring person, guidance for setting a sample and closing the sample-chamber lid after setting the sample is displayed.

(Step S48) As the measuring person sets a sample in the sample chamber and closes the sample-chamber lid, the opening-closing information detected by the sample-chamber lid opening-closing detecting means 13 is shifted to closing, thereby going to Step S50. When the sample-chamber lid is in an opening state, the process goes to Step S49.

(Step S49) Closing of the sample-chamber lid is monitored using the sample-chamber lid opening-closing detecting means 13.

(Step S50) When closing of the sample-chamber lid 12 is detected by the sample-chamber lid opening-closing detecting means 13, the lamp is turned on and data acquisition of stability monitoring is started.

(Step S51) When it is determined to be stable as an obtained value of the stability monitoring satisfies the stability determination conditions inputted for the instructions, the process goes to Step S52, and the obtained value does not satisfy the stability determination conditions, the stability monitoring is continued.

(Step S52) Data acquisition of the stability monitoring is ended. Steps following Step S53 are the same as those in the other embodiments.

Here, an embodiment of the stability monitoring indicated in Steps S50 to S52 will be described. In the stability monitoring, the time change measurement capable of measuring changes of the measured value over time at a regular interval with a fixed wavelength is started by the spectrophotometer. Here, the data acquiring interval is preferable to be a small value within 1 s. The wavelength used in the time change measurement is tuned to a wavelength to be used in a sample measurement later. As an obtained value, absorbance, transmissivity, and reflectivity calculated using energy values obtained by the sample-side detector 14 and the reference-side detector 15, a sample-side energy value (light amount) obtained by the sample-side detector 14 and a reference-side energy value (light amount) obtained by the reference-side detector 15 can be used. In the single beam system and the ratio beam system, the absorbance, transmissivity, reflectivity, and sample-side energy value can be used. In the double beam system, in addition to the absorbance, transmissivity, reflectivity and sample-side energy value, since the sample is easily resolved by light, the reference-side energy value can also be used when the absorbance, transmissivity, and reflectivity of the sample are changed over time.

Figure 5:
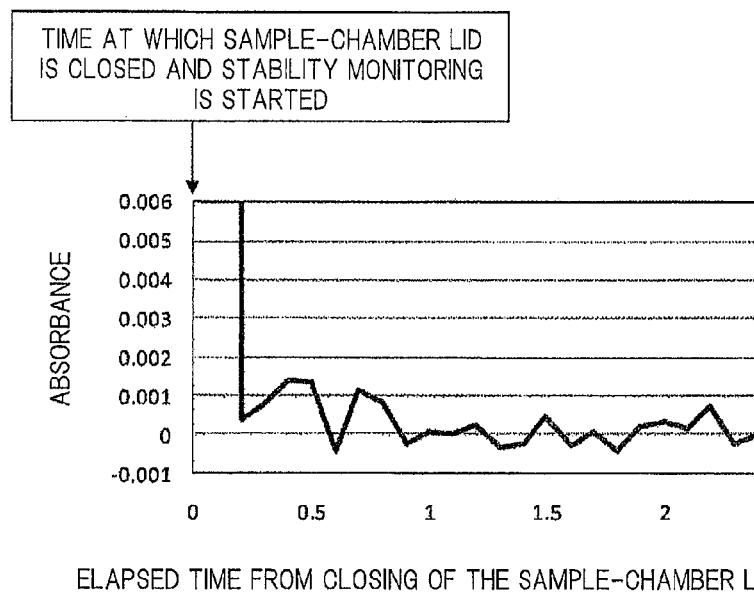
FIG. 5 is a diagram of a result of performing a time change measurement of absorbancy after closing a sample-chamber lid.

Data of the time change measurement of absorbance after closing the sample-chamber lid in the double beam system is illustrated in FIG. 5. From 0 s to 0.2 s after starting the time change measurement, it can be understood that the detector is not stable because the measurement is started immediately after closing the sample-chamber lid. Then, from 0.2 s to 1.0 s, it can be understood that the absorbance is significantly changed as the absorbance of −0.0004 to 0.0014 is obtained. It can be understood that the fluctuation in absorbance after 1.0 s is within a certain range. Such a tendency is found in the time change measurement data of absorbance obtained after closing the sample-chamber lid. As to the determination of stability, for example, the following methods are conceivable: a method of determining that the stability determination conditions are satisfied when a measured value within a range of the upper limit and lower limit inputted for instructions as the stability determination conditions is obtained in accordance with the accuracy of the measurement required by the measuring person; and a method of determining that the stability determination conditions are satisfied when a difference from the data-acquired point before the time change measurement is obtained and a difference within the range of the upper limit and lower limit inputted for instructions as the stability determination conditions is obtained in accordance with the accuracy of the measurement required by the measuring person.

Figure 6:
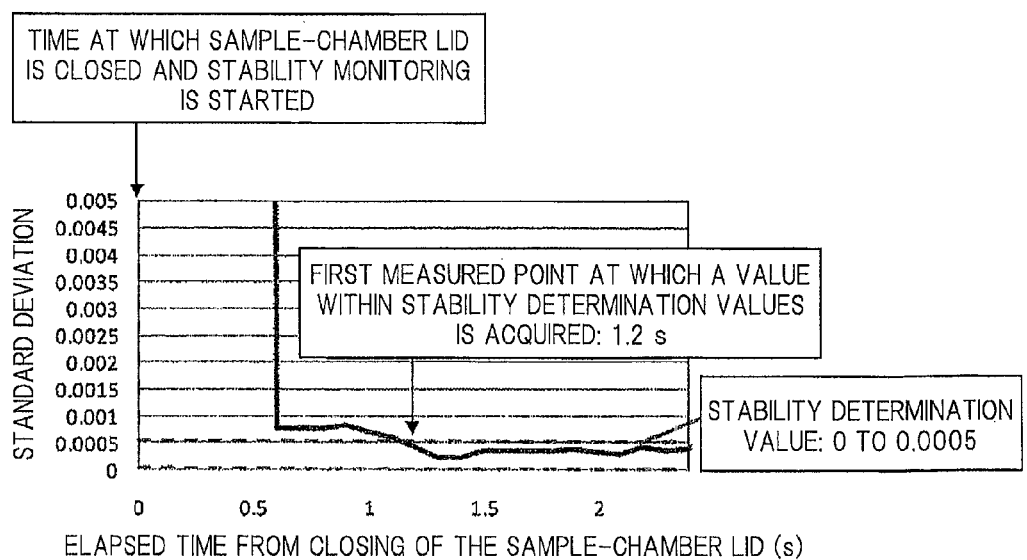
FIG. 6 is a diagram of a stability level determination that is performed using a standard deviation calculated from the past five points of absorbancy obtained after closing the sample-chamber lid.

In addition, the case of calculating a standard deviation and making a determination will be described with reference to FIG. 6. In FIG. 6, using the values obtained in FIG. 5, measured values of the past 'n' points (here, five points) inputted for instructions are used to calculate a value of standard deviation and the standard deviation is graphically shown together with the elapsed time from the closing of the sample-chamber lid. It can be understood that along with the elapsed time from the closing of the sample-chamber lid, the obtained value of standard deviation becomes smaller. When a standard deviation within a range of the upper limit and lower limit inputted for instructions as the stability determination conditions is obtained in accordance with accuracy of the measurement required by the measuring person beforehand, it can be determined that the stability determination conditions are satisfied. In the example of FIG. 6, when standard deviations of 0.0005 at the upper limit and of 0 at the lower limit are inputted for instructions as the stability determination conditions, it can be determined that the stability determination conditions are satisfied at 1.2 s at which a standard deviation within the range is first obtained. In addition to that, in the case in which measured points within the range of the stability determination conditions are entered for the specified number of times, and in the case in which measured points within the range of the determination conditions are sequentially entered for the number of times specified by the measuring person, it can be determined that the stability determination conditions are satisfied. As to the transmissivity and reflectivity, the same determination method as that of the absorbance can be used.

Figure 7:
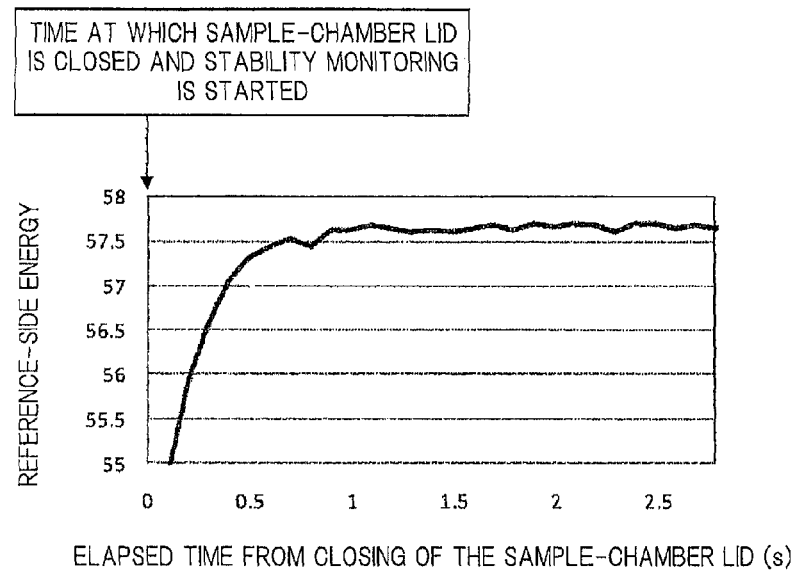
FIG. 7 is a diagram of a result performing a time change measurement of an energy value on a reference side after closing the sample-chamber lid.

Data of a time change measurement of the reference-side energy value performed after closing the sample-chamber lid in the double beam system is illustrated in FIG. 7. This system is used in the case in which absorbance, transmissivity, and reflectivity of a sample are changed as the sample is chemically and physically changed due to the measurement light and thus stability of the measurement cannot be determined. In FIG. 7, "from 0 s to 0.9 s" after starting the time change measurement indicates the time immediately after closing the sample-chamber lid, it can be understood that the reference-side detector is not stable. It can be understood to be within a certain range after 1.0 s. Since such a tendency is found in the reference-side energy, as to the determination of stability, in the same manner as the absorbance, the following methods are conceivable: a method of determining that the stability determination conditions are satisfied when a measured value within a range of the upper limit and lower limit inputted for instructions as the stability determination conditions is obtained in accordance with the accuracy of the measurement required by the measuring person; and a method of determining that the stability determination conditions are satisfied when a difference from the data-acquired point before the time change measurement is obtained and a difference within the range of the upper limit and lower limit inputted for instructions as the stability determination conditions is obtained in accordance with the accuracy of the measurement required by the measuring person.

Figure 8:
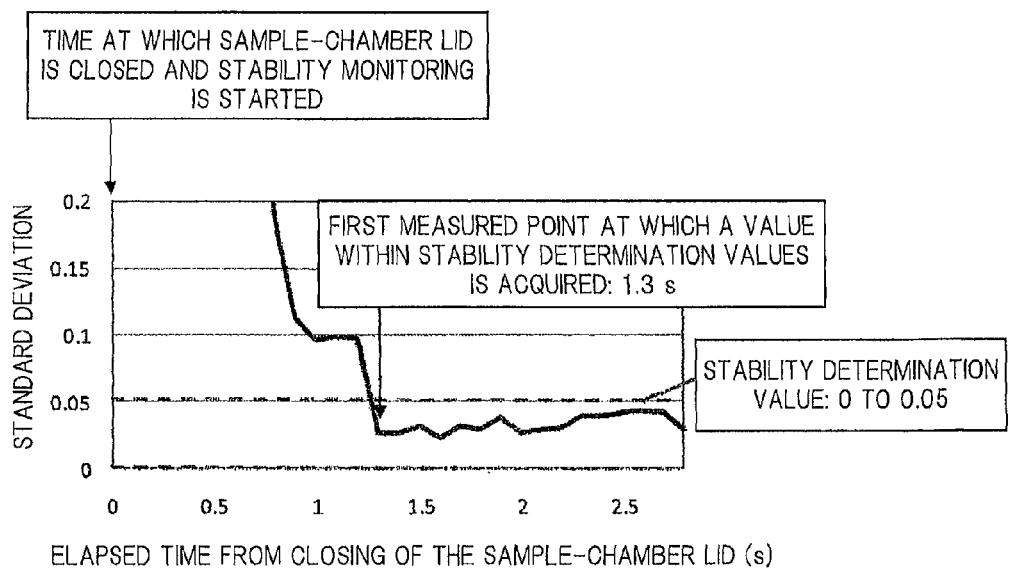
FIG. 8 is a diagram of a stability level determination that is performed using a standard deviation of the past five points of energy values on the reference side obtained after closing the sample-chamber lid.

In addition, the case of calculating a standard deviation and making a determination will be described with reference to FIG. 8. In FIG. 8, using the values obtained in FIG. 7, measured values of the past 'n' points (here, five points) inputted for instructions are used to calculate a value of standard deviation and the standard deviation is graphically shown together with the elapsed time from the closing of the sample-chamber lid. It can be understood that along with the elapsed time from the closing of the sample-chamber lid, the obtained value of standard deviation becomes smaller. When a standard deviation within a range of the upper limit and lower limit inputted for instructions as the stability determination conditions is obtained in accordance with accuracy of the measurement required by the measuring person beforehand, it can be determined that the stability determination conditions are satisfied. In the example of FIG. 8, when standard deviations of 0.05 at the upper limit and of 0 at the lower limit are inputted for instructions as the stability determination conditions, it can be determined that the stability determination conditions are satisfies at 1.3 s at which a standard deviation within the range is first obtained. In addition to that, in the case in which measured points within the range of the stability determination conditions are entered for the specified number of times, and in the case in which measured points within the range of the determination conditions are sequentially entered for the number of times specified by the measuring person, it can be determined that the stability determination conditions are satisfied. In the case in which the sample-side energy value is used, the same determination method can be used. This stability determination described in the third embodiment can also be used in the second embodiment.

Figure 9:
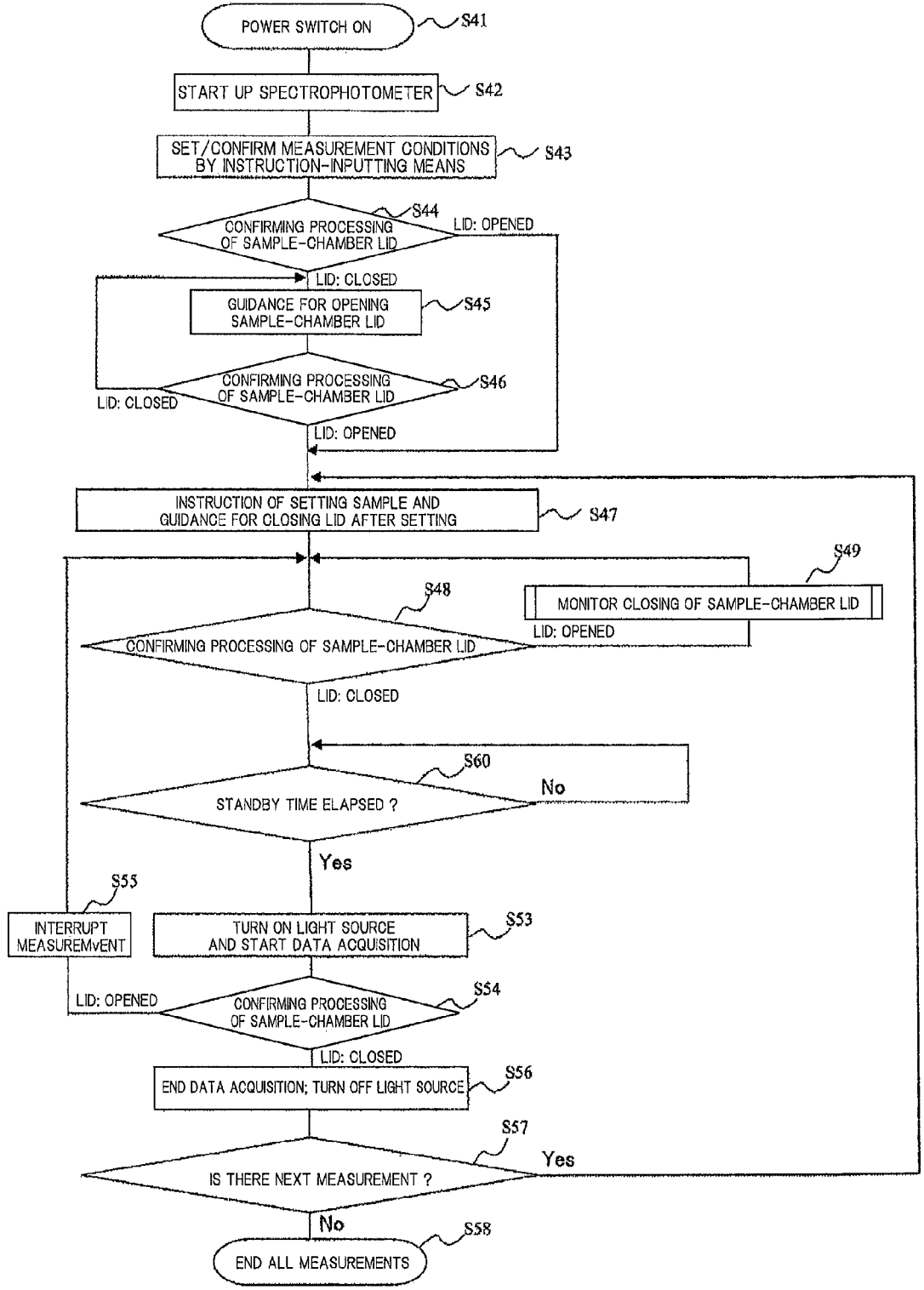
FIG. 9 is a flowchart of a control processing executed by a processor/storage device according to a fourth embodiment of the present invention.

FIG. 9 is a flowchart of a measurement control processing executed by a processor/storage device according to a fourth embodiment of the present invention. FIG. 9 is a method of using Step S60 instead of the stability monitoring of Steps S50 to S52 in FIG. 4. Hereinafter, Step S60 will be described.

(Step S60) When the sample-chamber lid opening-closing detecting means 13 detects closing of the sample-chamber lid in Step S48, the standby time inputted by the instruction-inputting means in Step S43 or the standby time stored in the storage device previously inputted for instructions as a fixed value is waited for. When the standby time is elapsed, the process goes to Step S53. A method of determining the standby time here is to set a time confirmed to be sufficiently stable as determined from actually measured data using the method described in Steps S50 to S52. The following two standby times are conceivable: one is fixed by one condition in accordance with a previous consideration, and the other one is optionally and freely changed by the measuring person. The stability determination described in the fourth embodiment can also be used in the second embodiment.

As described above, according to the embodiments, by mounting a xenon flash tube with low heat generation to a light-source part of the spectrophotometer and working the sample-chamber lid opening-closing detecting means and turning on and off of the light source in cooperation, the light source is turned on and the measurement is made impossible when the sample-chamber lid is being opened, and turning on of the light source is made possible when the sample-chamber lid is being closed, thereby obtaining the effects of increase of a usable period of the light source and a reduction in power consumption. In addition, the measuring person can start the measurement by closing the sample-chamber lid without instructing start of the measurement, and also the measured value obtained by the spectrophotometer is stabilized and thus an accurate measured value can be obtained. The present patent can be practiced as long as the lamp is of a low heat generating type such as an LED light source.

EXPLANATION OF REFERENCE NUMERALS

1 Light source;
2 Spectrometer;
3 Beam splitter;
4 Sample-side light flux;
5, 6, 7 Reflecting Mirror;
8 Reference-side light flux;
9 Sample setting part;
10 Reference-sample setting part;
11 Sample chamber;
12 Sample-chamber lid;
13 Sample-chamber lid opening-closing detecting means;
14 Sample-side detector;
15 Reference-side detector;
16 Sample-side AMP/AD converter;
17 Reference-side AMP/AD converter;
18 Processor/storage device;
19 Detection signal of opening-closing of sample-chamber lid;
20 Apparatus control signal;
21 Display signal;
22 Display part; and
23 Instruction-inputting means

What is claimed is:

1. A spectrophotometer comprising:
    a sample-chamber lid configured to open and close an opening portion of a sample chamber for setting a sample and a reference sample;
    a sample-chamber lid opening-closing detector configured to detect an opening-closing state of the sample-chamber lid;
    a xenon flash tube as a light source;
    a spectrometer;
    a detector configured to detect transmitted light;
    an amplifier and an analog to digital (AD) converter;
    a processor coupled to a storage device storing predetermined stability determination conditions; and
    a display,
    wherein the spectrometer, the light source, the detector, the amplifier, the AD converter, and the display are coupled to the processor, the processor configured to:
    upon detecting that a state of the lid changes from an opening state to a closing state based on detection signals from the sample-chamber lid opening-closing detector, control the light source to emit light at a predetermined wavelength and control the detector to detect transmitted light, and simultaneously measure absorbance values at regular time intervals based on detection signals transmitted by the detector and amplified and converted by the AD converter,
    determine whether the predetermined stability determination conditions are satisfied based on the measured absorbance values at the regular time intervals,
    upon determining, based on the measured absorbance values at the regular time intervals, that the predetermined stability determination conditions are satisfied, control the light source to continue to emit light at the predetermined wavelength and control the detector to detect transmitted light and measure at least one of absorbency, transmissivity, reflectivity, and a sample-side energy value, based on detection signals transmitted by the detector and amplified and converted by the AD converter, to obtain a measurement result of the sample, and
    control the display to display the measurement result.

2. The spectrophotometer according to claim 1,
    wherein the measurement of the absorbance values is interrupted after a state of the lid changing from a closing state to an opening state is detected.

3. The spectrophotometer according to claim 1,
    wherein an upper limit and a lower limit of absorbance values of the predetermined stability determination conditions are stored in the storage device,
    wherein the processor is configured to determine whether the predetermined stability determination conditions are satisfied based on whether the measured absorbance values at the regular time intervals are within the upper limit and the lower limit.

4. The spectrophotometer according to claim 3,
    wherein the processor is configured to determine whether the predetermined stability determination conditions are satisfied based on whether a difference of the measured absorbance values at the regular time intervals at a current measured point and a previous measured point of are within the range between the upper limit and the lower limit of the stability determination conditions.

5. The spectrophotometer according to claim 3,
    wherein the processor is configured to whether the predetermined stability determination conditions are satisfied based on whether a time when a standard deviation from the previous measured points to the current measured point the standard deviation is acquired within a predetermined range.

6. The spectrophotometer according to claim 1, wherein an LED is used as a light source.

* * * * *